US006432107B1

(12) United States Patent
Ferree (10) Patent No.: US 6,432,107 B1
(45) Date of Patent: Aug. 13, 2002

(54) ENHANCED SURFACE AREA SPINAL FUSION DEVICES

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/483,805

(22) Filed: Jan. 15, 2000

(51) Int. Cl.$^7$ ............................................. A61B 17/70
(52) U.S. Cl. ..................................... 606/61; 623/17.11
(58) Field of Search ........ 606/61, 90; 623/17.11–17.16

(56) References Cited

U.S. PATENT DOCUMENTS

| | | | | |
|---|---|---|---|---|
| 4,743,256 A | | 5/1988 | Brantigan | 623/17 |
| 4,834,757 A | * | 5/1989 | Brantigan | 623/17.11 |
| 5,425,772 A | | 6/1995 | Brantigan | 623/17 |
| 5,522,899 A | | 6/1996 | Michelson | 623/17 |
| 5,554,191 A | | 9/1996 | Lahille et al. | 623/17 |
| 5,591,235 A | | 1/1997 | Kuslich | 623/17 |
| 5,609,635 A | | 3/1997 | Michelson | 623/17 |
| 5,658,335 A | | 8/1997 | Allen | 623/17 |
| 6,143,033 A | * | 11/2000 | Paul et al. | 623/17.11 |

* cited by examiner

Primary Examiner—Nicholas D. Lucchesi
Assistant Examiner—Michael B. Priddy

(74) Attorney, Agent, or Firm—Gifford, Krass, Groh, Sprinkle, Anderson & Citkowski, PC (57) ABSTRACT

Enhanced surface area spinal fusion devices have upper and lower sections which are implanted directly within the bodies of the vertebrae being fused, thereby surrounding the implanted sections with cancellous bone which is more conducive to ingrowth and permanent fusion. A preferred device comprises a frame-like structure composed of biocompatible material such as carbon fiber, the structure having a substantially hollow interior and open side walls or apertures to receive bone-graft material. The device is preferably used in conjunction with adjoining intervertebral cages, which may be rigidly joined to one another and/or to the inventive device. One or more physical features are also preferably provided to engage with surrounding bone or minimize back-out, such features including teeth, ridges, grooves, or outriggers. One or more shape-memory elements may also be used, each of which is preferably compressed for insertion then expanded when the device is in place. The inventive fixation device need not be employed between adjacent vertebra, but may be used between vertebra separated by one or more intermediate vertebra, in which case the device extends through the intermediate vertebra, preferably in intimate contact therewith. Multiple devices may also be implanted side by side between the same set of adjacent vertebra. In addition to these various alternative embodiments of the invention, a preferred method if installation is also disclosed.

22 Claims, 6 Drawing Sheets

ENHANCED SURFACE AREA SPINAL FUSION DEVICES

FIELD OF THE INVENTION

This invention relates generally to corrective spinal surgery and, in particular, to vertebral fusion devices providing a greater surface area to enhance fusion.

BACKGROUND OF THE INVENTION

In conjunction with spinal surgery, interbody fusion cages are regularly placed between the endplates of the vertebrae to aid in fusion. This is justified on the basis that the end plates of the vertebrae are stronger than the cancellous bone within the body of the vertebrae, enabling the strength of the end plates to be relied upon for distraction. Such distraction restores the disc space height, thereby hopefully alleviating pressure on the spinal nerves and, hopefully, reducing pain or discomfort, if present.

Fusion is more successful if done in cancellous bone, however. Thus, when performing interbody fusion, the surgeon must balance preserving the end plates for support while removing at least a portion thereof to aid in fusion. To achieve this balance, the surgeon typically scraps or decorticates a portion of the opposing end plates to expose the underlying cancellous bone.

Figure 1A:
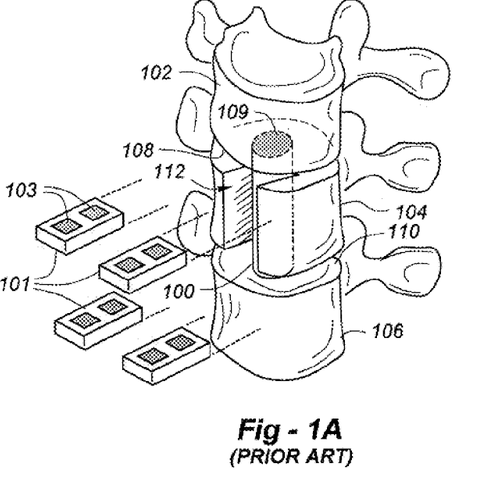
FIG. 1A is a drawing providing a perspective view of prior-art devices used for intervertebral fusion, including a strut graft and cages placed between vertebral end plates.
Figure 1B:
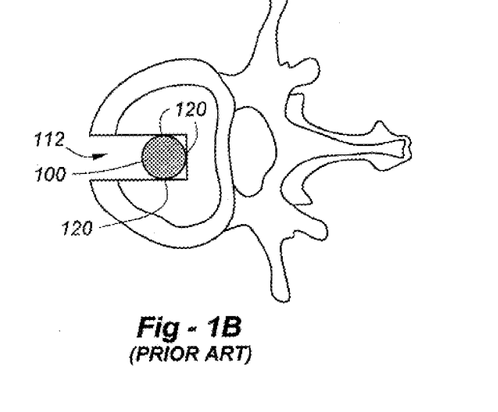
FIG. 1B is a cross-section of a vertebrae of FIG. 1A, showing the way in which the strut graft contacts a slot formed therethrough.

FIGS. 1A and 1B illustrate, from an oblique perspective, existing prior-art devices such as strut graft 100 and cages 101 used for distraction and/or fusion. It is important to note that, although FIG. 1A implies the use of strut graft 100 and cages 101 used in combination, they are used separately according to the current practice. That is, when a strut graft is used, cages are not, and when cages are used, they occupy the entire intervertebral space, thereby precluding the use of a strut graft. Nevertheless, both are shown in the figure as the alternatives currently in use. The strut graft 100 is typically an elongated body dimensioned to extend from the inferior end plate 108 of vertebrae 102 to the superior end plate 110 of vertebrae 106, also extending through an intermediate vertebrae 104 through a slot 112. Those of skill appreciate that longer members, penetrating through a plurality of slotted vertebrae are also in use. FIG. 1B illustrates the arrangement from a transverse section taken through vertebrae 104.

To install the graft 100, the channel 112 is formed into one or more intermediate vertebrae using chisels or power burrs. The walls formed through the vertebrae are accordingly irregular, reducing the likelihood of contact points 120 between the device 100 and the walls of the slot. As best seen in FIG. 1B, even if a perfectly rectangular slot were to be formed through intermediate vertebrae 104, the points of contact would be limited to points 120. The decreased contact area increases the likelihood of device migration and failure of fusion. In addition, only a small portion 109 of the inferior end plate 108 of vertebrae 102, and a correspondingly small portion (covered by the end of device) of superior end plate of vertebrae 106 is scraped away and allowed to fuse with the ends of the graft 100, the result being a structure which is less than optimal. The area for fusion adjacent to the endplates is even smaller with interbody fusion cages 103.

SUMMARY OF THE INVENTION

The subject of the present invention resides in enhanced surface area spinal fixation devices. Broadly, in contrast to existing intervertebral cages and strut grafts, which minimally penetrate the cortical endplates of the vertebra to be fused, devices according to the invention have upper and lower sections which are implanted directly within the bodies of the vertebra being fused, thereby surrounding the implanted sections with cancellous bone which is more conducive to ingrowth and permanent fusion.

In the preferred embodiment, a spinal fixation device according to the invention comprises a frame-like structure composed of biocompatible material such as carbon fiber, having a substantially hollow interior and open side walls, ends, or apertures to receive bone-graft material. The device is preferably used in conjunction with adjoining intervertebral cages, which may be rigidly joined to one another and/or to the inventive device. The cages rely on retained endplates for distraction. Wedge-shaped distraction plugs, similar to intervertebral cages, may alternatively be employed. Since fusion occurs through the device to enhance surface area, such plugs may be solid.

The spinal fixation device also preferably further includes one or more physical features to engage with surrounding bone or minimize back-out, such as teeth, ridges, grooves, or outriggers. One or more shape-memory elements may also be used, each of which is preferably compressed for insertion then expanded when the device is in place.

The inventive fixation device need not be employed between adjacent vertebra, but may be used between vertebra separated by one or more intermediate vertebra, in which case the device extends through the intermediate vertebra, preferably in intimate contact therewith. Multiple devices may also be implanted side by side between the same set of adjacent vertebra. In addition to these various alternative embodiments of the invention, a preferred method of installation is also disclosed.

DETAILED DESCRIPTION OF THE INVENTION

Figures 2A, 2B:
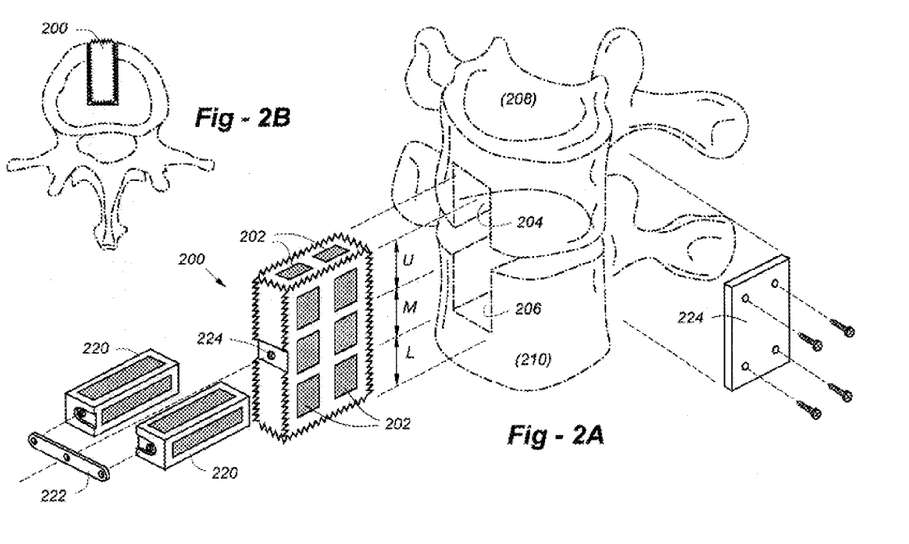
FIG. 2A is a drawing providing a perspective view of an enhanced surface area spinal fusion device according to the invention in conjunction with intervertebral cages and optional fixation devices.
FIG. 2B is a cross-section of a vertebrae of FIG. 2A, showing the enhanced surface area viewed from a top-down perspective.

Turning now to FIG. 2A, there is shown, from an oblique perspective, an enhanced surface area spinal fusion device according to the invention, generally at 200. The device is preferably frame-like having a lower section L, a middle M, and an upper section U. The device 200 further preferably comprises multiple passageways or apertures 202 into which bone-graft material may be placed to aid in fusion overall. Although the apertures 202 depicted in FIG. 2A are rectangular in shape, other geometries may be used, as appropriate, including circular and oval openings.

The device 200 fits into slots 204 and 206 made in upper and lower vertebrae 208 and 210, respectively, allowing the lower section to fuse within the body of the lower vertebrae 210, and the upper section to fuse within the body of the upper vertebrae 208. Thus, in contrast to existing devices, the device 200 and the alternative embodiments disclosed herein feature considerably more intimate contact with cancellous bone due to the fact that the device is inserted directly into the cavities 204 and 206. Rather than a relatively minor amount of scraping of the end plates of the vertebrae to be distracted, the entire end portions of the device 200 which penetrate the upper and lower vertebrae make contact with cancellous bone, thereby enhancing fusion considerably. FIG. 2B is a cross-section of a vertebrae of FIG. 2A as viewed from a top-down perspective, showing how the device fits tightly along the entire walls of the channels created in the vertebrae.

Figures 3A, 3B, 3C, 5J, 5K:
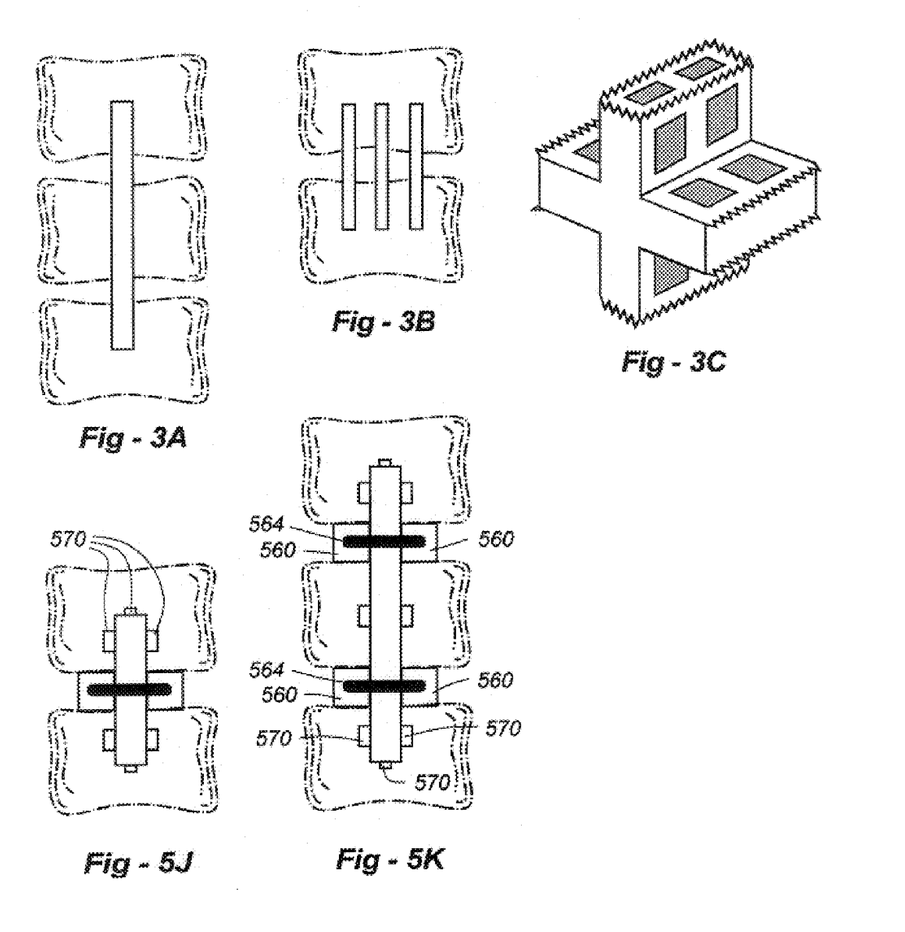
FIG. 3A is a schematic anterior-posterior view of an enhanced surface area fusion device according to the invention cooperating with three vertebrae.
FIG. 3B is a schematic anterior-posterior view of a plurality of devices according to the invention installed between adjacent vertebrae.
FIG. 3C is an oblique representation of a device according to the invention wherein an enhanced surface area device is integrally formed with side members obviating the need for separate intervertebral cages.
FIGS. 5A to 5K are drawings which show a preferred method resecting vertebrae through the installation of an enhanced surface area spinal fusion device according to the invention.

The device 200 is preferably constructed in the cage-like manner, allowing bone ingrowth material to be inserted into the openings at 202, thereby. further promoting ingrowth once installed. The teeth 216, ridges or other devices disclosed elsewhere herein further assist in engaging with bone to maintain stability. Other arrangements to prevent back-out discussed with reference to FIGS. 4A through 4D may also be used. Although the drawing of FIG. 2 shows the device 200 interposed between adjacent vertebra, it may fuse vertebrae which are not adjacent, in which case the intermediate vertebrae would be slotted from their superior to inferior surfaces, much like slot 112 of vertebrae 104 in FIGS. 1A and 1B. As shown in FIG. 3B, the invention is not limited to the use of a single device per vertebrae to be fused, but two or more devices may be used, each engaging with separate slots.

In contrast to existing strut grafts and cages, which are used separately and not in combination, the device 200 may be used with cages 220, preferably filled with bonegraft material. An optional transverse bar 222 may also be used, not only to fasten the cages 220 together, but a point of fastening 224 may be provided on the device 200 as well, forming an integral unit. Conventional intervertebral cages may be used or, alternatively, cages may be used of the type described in my co-pending U.S. patent application Ser. No. 09/454,908, the entire contents of which are incorporated herein by reference. As a further alternative, an enhanced surface area device may be integrally formed with side members acting as cages, resulting in the cruciate configuration of FIG. 3C. Additional fixation devices such as one or more plates 224, may be used to provide additional stability.

Devices according to the invention may be constructed of various materials, though, in the preferred embodiment, carbon fiber would be used. Whereas current struts are made of metal or bone, carbon fiber devices would allow x-ray determination of fusion to be more easily assessed. Devices according to the invention may, however, be composed of metal or bone and, if composed of bone, the aperture such as 202 would not need to be provided, since a solid piece of bone graft may be used. The device may also be covered with a bone ingrowth material such as titanium mesh or plasma spray. Plastic or ceramics may also be used, as appropriate.

Figure 4A:
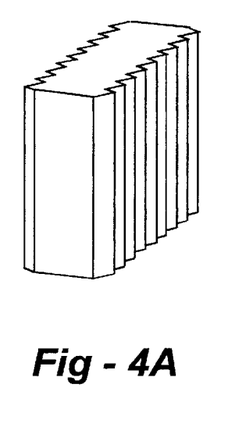
FIG. 4A is an oblique drawing which shows how elongated ridges may be used to minimize back-out of a device according to the invention.
Figure 4B:
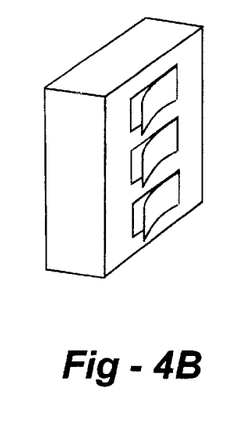
FIG. 4B is a drawing which shows how barbs, including shape-memory barbs may be used in conjunction with a device to minimize back-out.
Figure 4C:
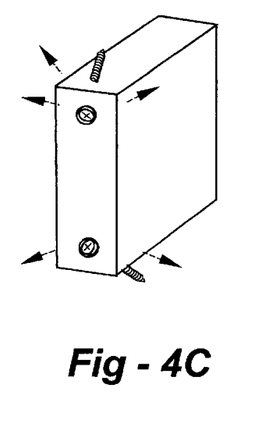
FIG. 4C is a drawing which shows how screws or other fasteners in different orientations may be used to fix an enhanced surface area device according to the invention in place.

As discussed above, various structures and mechanisms may be used to hold a device according to the invention in place. In addition to the preferred use of teeth 216 in FIG. 2A, one or more sides of the device may have ribs or ridges as shown in FIG. 4A to assist in preventing back-out. As an alternative, barbed projections or outriggers may be used as shown in FIG. 4B, and may incorporate spring-biased or shape-memory materials to ease insertion while allowing for expansion following introduction of the device. As shown in FIG. 4C, one or more screws may be used to fix the device medially-laterally or directly into the superior/posterior vertebrae being fused.

Figure 4D:
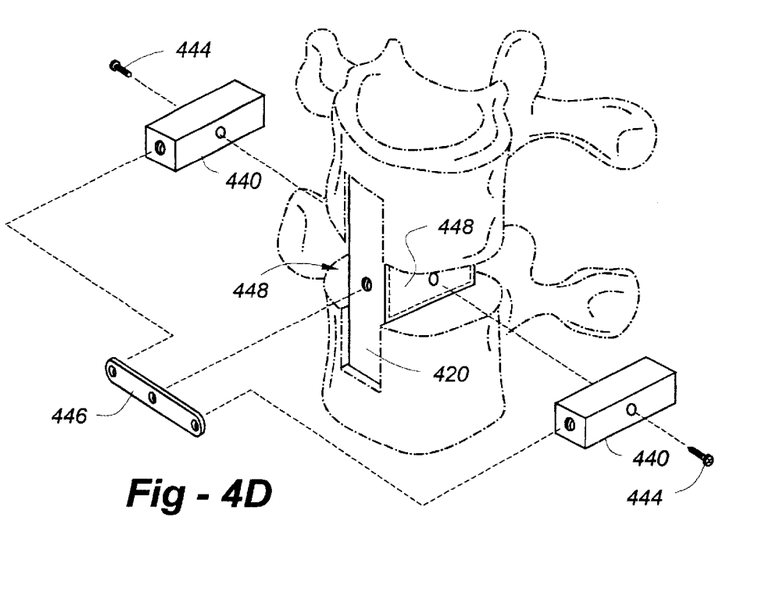
FIG. 4D is a drawing which shows the use of metal or plastic plugs, preferably made with a shape-memory material, which expands after implantation to hold an enhanced surface area device in place.

FIG. 4D illustrates the use of distraction plugs 440 according to the invention, wherein pieces of metal, plastic, bone or other suitable materials such as carbon fiber are attached to the sides of the device 420, either using fasteners such as screws 444, a transverse bar 446, or both. In a preferred embodiment, the plugs would be made of carbon fiber, whereas the transverse connector would preferably be made of titanium. As an alternative to a rigid material, the plugs may incorporate a shape-memory material, which would allow for easy insertion of device, but would prevent the device from backing out once installed. To assist in positioning, recesses 448 may be provided on either sides of the device 420. The plugs may be rectangular or wedge-shaped to account for lordosis, as described in my co-pending U.S. patent application referenced above.

FIGS. 5A through 5K illustrate preferred steps associated with the installation of a device according to the invention. Although the system is preferably designed for an anterior approach, the invention is not limited in this manner, and may be placed posteriority, with rods, screws, etc. applied through separate incisions, as appropriate.

Figures 5A, 5B:
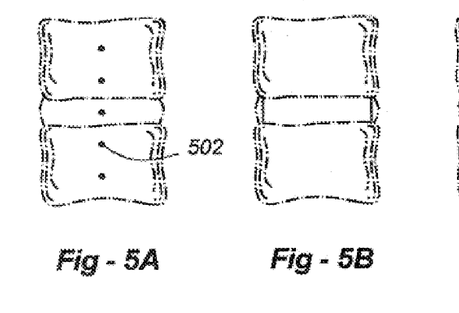
Figure 5C:
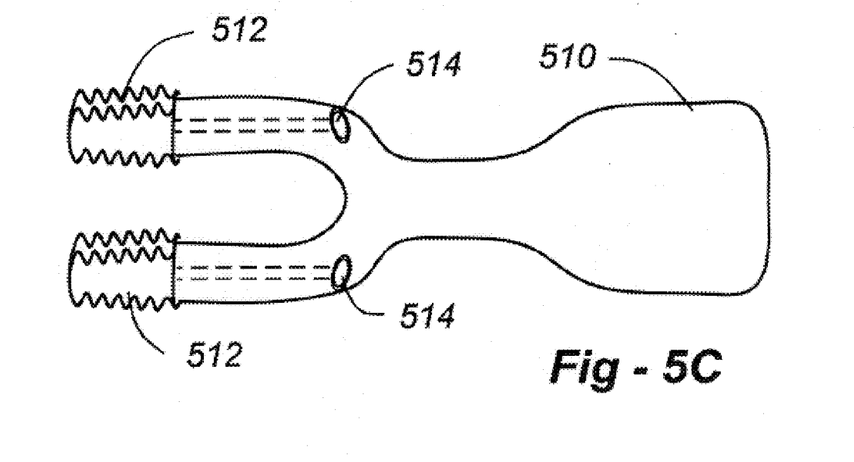
Figures 5D, 5F:
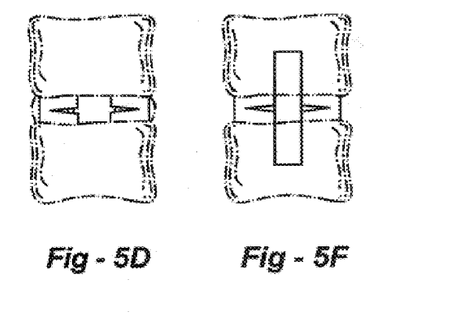

FIG. 5A is a drawing which shows how a midline 502 would first be determined using fluoroscopy. As shown in FIG. 5B, the anterior annulus and nucleus pulpous or, at least a portion of the nucleus would be removed for distraction and insertion of the inventive device. FIG. 5C is a simplified drawing which shows an insertion tool 510 used to install distracters 512. Such a device preferably includes screws 514 to hold the distracter to the insertion tool until it is removed. FIG. 5D shows the distracters in place medially and laterally between adjacent vertebrae.

Figure 5E:
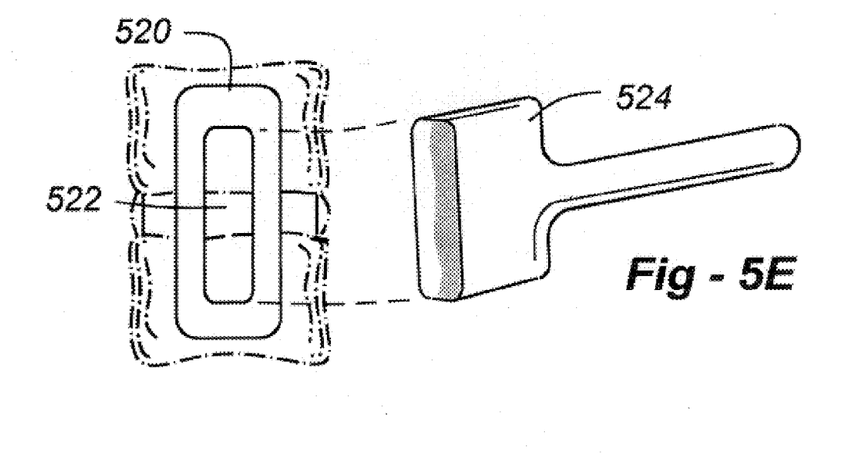

In FIG. 5E, a guide 520 has been installed over adjacent vertebrae which is used including a slot 522 to receive a device such as box chisel 524. Other instruments such as a bone saw may be used, but in any case, stops are used to ensure that the channel has a depth preferably in the range of 15–30 mm. FIG. 5F illustrates a rectangular shaped slot formed between adjacent vertebrae once the box chisel 524 of FIG. 5E has been removed. To perform the posterior cuts and remove the pieces, a tool such as that shown in FIG. 5G having cutting edges 540 and depth stops 541 is preferably used. When the handles 542 of the tool are squeezed, the cutting edges are away from one another, allowing them to resect bone above and below.

Figure 5G:
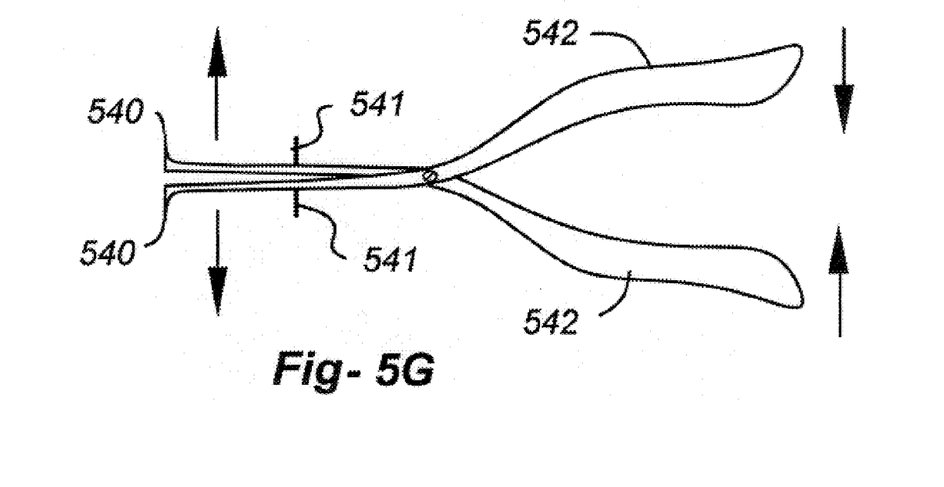
Figure 5H:
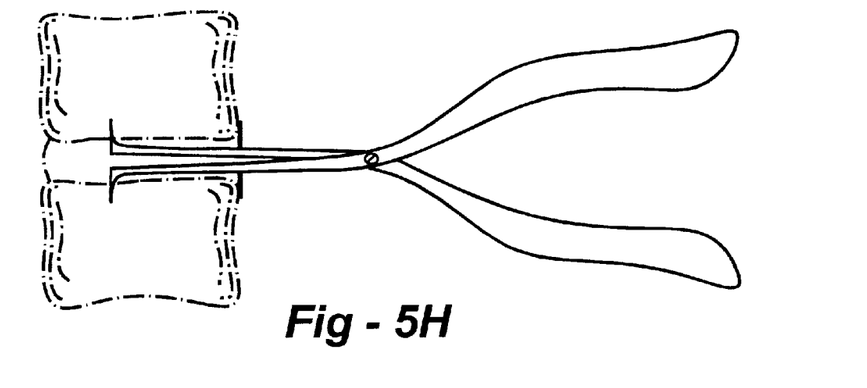
Figure 5I:
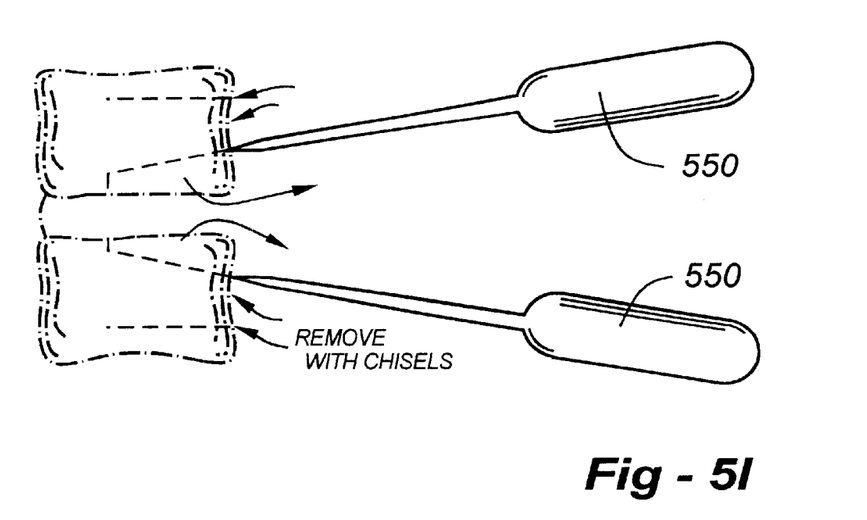

FIG. 5H is a side-view drawing showing the tool of FIG. 5G in place, with the distraction plugs removed for clarity of illustration. FIG. 5I is a side-view drawing illustrating how the pieces of cut bone would preferably be removed with a saw or box chisel. In particular, a cutting tool such as an osteotome 550 would be used to progressively penetrate the anterior wall and, by tapping the cutting blade posteriority, slices may be formed and removed until the final slots are formed. Care must be taken so as not to disturb the final cuts, however. The device is then inserted, as shown in FIG. 5J, and additional fixation devices are used, as described elsewhere hereinabove to prevent back-out. FIG. 5K is a drawing providing a perspective view of a multilevel spinal fusion device according to the invention with distraction plugs or intervertebral cages (shown as 560), transverse connectors 564, and element 570 to prevent back-out.

In addition to the enhanced surface area made possible by the invention for fixation, another advantage is that the bone material removed to form the slots as just described may be used to fill the device, obviating the need to harvest additional bone from the patient. Harvesting bone graft is painful, typically delays a patient's recovery, and could cause complications such as fracture, infection or nerve injury.

I claim:

1. An enhanced surface area spinal fusion device adapted for use between an upper vertebral body having an inferior vertebral endplate and a lower vertebral body having a superior endplate, wherein the interior of each body is composed of cancellous bone and each endplate is composed of cortical bone, with the distance between the endplates defining at least one intervertebral spacing, the device comprising:

biocompatible structure having an outer surface conducive to bone ingrowth and two end surfaces; and wherein the structure is composed of one or more pieces of natural bone taken from the upper and lower bodies having been modified to receive the structure and the end surfaces of the structure define a height which is greater than the intervertebral spacing, such that when implanted, at least a portion of the device extends substantially beyond the superior endplate, the inferior endplate, or both, thereby penetrating into one or both of the upper and lower vertebra bodies and through the cortical bone, such that the end surface and outer surface of the penetrating portion are surrounded by cancellous bone.

2. The spinal fusion device of claim 1, wherein the structure is frame-like, including a substantially hollow interior to receive bone-graft material.

3. The spinal fusion device of claim 1, wherein the structure is composed of a carbon-fiber material.

4. An enhanced surface area spinal fusion device adapted for use between an upper vertebral body having an inferior vertebral endplate and a lower vertebral body having a superior endplate, wherein the interior of each body is composed of cancellous bone and each endplate is composed of cortical bone, with the distance between the endplates defining at least one intervertebral spacing, the device comprising:

a biocompatible structure having an outer surface conducive to bone ingrowth and two end surfaces defining a height which is greater than the intervertebral spacing, such that when implanted, at least a portion of the device extends substantially beyond the superior endplate, the inferior endplate, or both, thereby penetrating into one or both of the upper and lower vertebral bodies and through the cortical bone, such that the end surface and outer surface of the penetrating portion arm surrounded by cancellous bone; and one or more distraction devices positioned between the vertebral endplates.

5. The spinal fusion of claim 4, wherein the distraction devices are plugs attachable to one or more sides of the structure.

6. The spinal fusion device of claim 4, wherein the distraction devices include at least one intervertebral cage.

7. The spinal fusion device of claim 6, further including a member for rigid attachment of each cage to the structure.

8. An enhanced surface area spinal fusion device adapted for use between an upper vertebral body having an inferior vertebral endplate and a lower vertebral body having a superior endplate, wherein the interior of each body is composed of cancellous bone and each endplate is composed of cortical bone, with the distance between the endplates defining at least one intervertebral spacing, the device comprising:

a biocompatible structure having an outer surface conducive to bone ingrowth and two end surfaces defining a height which is greater than the intervertebral spacing, such that when implanted, at least a portion of the device extends substantially beyond the superior endplate, the inferior endplate, or both, thereby penetrating into one or both of the upper and lower vertebral bodies and through the cortical bone, such that the end surface and outer surface of the penetrating portion are surrounded by cancellous bone; and one or more intervertebral cages integrally formed with the device.

9. An enhanced surface area spinal fusion device adapted for use between an upper vertebral body having an inferior vertebral endplate and a lower vertebra body having a superior endplate, wherein the interior of each body is composed of cancellous bone and each endplate is composed of cortical bone, with the distance between the endplates defining at least one intervertebral spacing, the device comprising:

a biocompatible structure having an outer surface conducive to bone ingrowth and two end surfaces defining a height which is greater than the intervertebral spacing, such that when implanted, at least a portion of the device extends substantially beyond the superior endplate, the inferior endplate, or both, thereby penetrating into one or both of the upper and lower vertebral bodies and through the cortical bone, such that the end surface and outer surface of the penetrating portion are surrounded by cancellous bone; and one or more physical features to engage with surrounding bone to minimize back-out, at least one shape memory element which is compressed for insertion of the device and expanded when the device is in place.

10. The spinal fusion device of claim 9, wherein the physical features includes one or more teeth, ridges, grooves, or outriggers extending from the outer surface.

11. An enhanced surface area spinal fusion device adapted for use between an upper vertebral body having an inferior vertebral endplate and a lower vertebral body having a superior endplate, wherein the interior of each body is composed of cancellous bone and each endplate is composed of cortical bone, with the distance between the endplates defining at least one intervertebral spacing, the device comprising:

a biocompatible structure having an outer surface conducive to bone ingrowth and two end surfaces defining a height which is greater than the intervertebral spacing, such that when implanted, at least a portion of the device extends substantially beyond the superior endplate, the inferior endplate, or both, thereby penetrating into one or both of the upper and lower vertebral bodies and through the cortical bone, such that the end surface and outer surface of the penetrating portion are surrounded by cancellous bone; and wherein the structure extends through one or more intermediate vertebra located between the upper and lower vertebra.

12. A system for promoting fusion between an upper vertebra having an inferior vertebral endplate and a lower vertebra having a superior endplate, the distance between the endplates defining at least one intervertebral spacing, the system comprising:

a biocompatible strut having an outer surface conducive to bone ingrowth and a height which is at least slightly greater than the intervertebral spacing, such that when the device is installed between the upper and lower vertebra, at least a portion of the device extends beyond the superior endplate, the inferior endplate, or both, thereby penetrating into cancellous bone; and one or more distraction devices positioned adjacent the strut without penetrating the vertebral endplates.

13. The system of claim 12, wherein the distraction devices are plugs attachable to one or more sides of the strut.

14. The system of claim 12, wherein the distraction devices are substantially hollow intervertebral cages.

15. The system of claim 12, further including a rigid member for rigidly attaching each distraction device to the strut.

16. The system of claim 12, wherein each distraction device is integrally formed with the strut.

17. The spinal fusion device of claim 12, wherein the strut extends through one or more intermediate vertebra located between the upper and lower vertebra.

18. A method of promoting the fusion between upper and lower vertebra, each vertebra having a body between superior and inferior endplates, the method comprising the steps of:

providing the structure of claim 1;

removing an anterior section of the upper vertebra, including a portion of its inferior endplate;

removing an anterior section of the lower vertebra, including a portion of its superior endplate; and installing the structure between the vertebra using an anterior approach so as to substantially consume the removed sections.

19. The method of claim 18, wherein:

the upper and lower vertebra are not adjacent to one another, but instead are separated from one another by one or more intermediate vertebra, the method further including the step of:

removing an anterior section of each intermediate vertebra, including a portion of each endplate to receive the device therethrough.

20. The method of claim 18, further including the step of installing a plurality of structures placed side-to-side.

21. The method of claim 18, further including the step of installing a distraction device on either side of the device.

22. The method of claim 21, further including the step of rigidly attaching each distraction device to the structure.

* * * * *

UNITED STATES PATENT AND TRADEMARK OFFICE
CERTIFICATE OF CORRECTION

PATENT NO. : 6,432,107 B1
DATED : August 13, 2002
INVENTOR(S) : Bret A. Ferree

It is certified that error appears in the above-identified patent and that said Letters Patent is hereby corrected as shown below:

<u>Title page,</u>
Item [57], ABSTRACT,
Line 25, replace "if" with -- of --.

<u>Column 4,</u>
Line 37, replace "of device" with -- of the device --.
Line 47, replace "posteriority" with -- posteriorily --.

<u>Column 5,</u>
Line 12, replace "posteriority" with -- posteriorily --.

<u>Column 6,</u>
Line 8, replace "arm" with -- are --.

Signed and Sealed this

Eighth Day of April, 2003

JAMES E. ROGAN
*Director of the United States Patent and Trademark Office*